US010792400B2

(12) United States Patent
Moon et al.

(10) Patent No.: US 10,792,400 B2
(45) Date of Patent: *Oct. 6, 2020

(54) MICROSTRUCTURE FORMULATION TECHNIQUES FOR BOTULINUM TOXIN

(71) Applicants: Hugel Inc., Gangwon-do (KR); Small Lab Co., Ltd., Daejeon (KR)

(72) Inventors: Kyeong Yeop Moon, Gangwon-do (KR); Chang Jin Lee, Seoul (KR); Dae Gun Kim, Gyeonggi-do (KR); Dong Hoon Oh, Gangwon-do (KR); Do Hyun Kang, Seoul (KR); Woo Ran Lee, Gangwon-do (KR); Jeong Gyu Lee, Daejeon (KR); Jun Jin Yoon, Gyeonggi-do (KR); Juhyung Shin, Gyeonggi-do (KR)

(73) Assignees: Hugel Inc., Gangwon-do (KR); Small Lab Co., Ltd., Daejeon (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/689,568

(22) Filed: Nov. 20, 2019

(65) Prior Publication Data

US 2020/0121831 A1 Apr. 23, 2020

Related U.S. Application Data

(63) Continuation-in-part of application No. 15/730,969, filed on Oct. 12, 2017, now Pat. No. 10,525,111.

(51) Int. Cl.
| | | |
|---|---|---|
| A61K 47/02 | (2006.01) | |
| A61K 9/02 | (2006.01) | |
| A61K 47/32 | (2006.01) | |
| A61K 47/20 | (2006.01) | |
| A61K 47/36 | (2006.01) | |
| A61L 31/04 | (2006.01) | |
| A61L 31/10 | (2006.01) | |
| A61M 37/00 | (2006.01) | |

(52) U.S. Cl.
CPC ............ *A61L 31/047* (2013.01); *A61L 31/10* (2013.01); *A61M 37/0015* (2013.01)

(58) Field of Classification Search
CPC ............ A61K 2300/00; A61K 31/137; A61K 31/222; A61K 31/4174; A61K 31/4415; A61K 45/06; A61K 31/20; A61K 31/428; A61K 39/3955; A61K 2039/505; A61K 2039/5258; A61K 2039/54; A61K 2039/55522; A61K 2039/55572; A61K 2039/6037; A61K 2039/627; A61K 31/519; A61K 38/47; A61K 39/07; A61K 39/12; A61K 39/385; A61K 39/395; A61K 47/10; A61K 47/12; A61K 47/14; A61K 47/26; A61K 8/4953; A61K 9/0014; A61K 9/7084; A61K 9/7092
See application file for complete search history.

(56) References Cited

U.S. PATENT DOCUMENTS

| | | |
|---|---|---|
| 5,437,291 A | 8/1995 | Pasricha et al. |
| 5,670,484 A | 9/1997 | Binder |
| 5,714,468 A | 2/1998 | Binder |
| 5,766,605 A | 6/1998 | Sanders et al. |
| 5,989,545 A | 11/1999 | Foster et al. |
| 6,063,768 A | 5/2000 | First |
| 6,113,915 A | 9/2000 | Aoki et al. |
| 6,139,845 A | 10/2000 | Donovan |
| 6,143,306 A | 11/2000 | Donovan |
| 6,261,572 B1 | 7/2001 | Donovan |
| 6,265,379 B1 | 7/2001 | Donovan |
| 6,299,893 B1 | 10/2001 | Schwartz et al. |
| 6,306,423 B1 | 10/2001 | Donovan et al. |
| 6,312,708 B1 | 11/2001 | Donovan et al. |
| 6,365,164 B1 | 4/2002 | Schmidt |
| 6,423,319 B1 | 7/2002 | Brooks et al. |
| 6,447,787 B1 | 9/2002 | Gassner et al. |
| 6,458,365 B1 | 10/2002 | Aoki et al. |
| 6,464,986 B1 | 10/2002 | Aoki et al. |
| 6,623,742 B2 | 9/2003 | Voet |
| 6,667,041 B2 | 12/2003 | Schmidt |
| 2002/0138049 A1 | 9/2002 | Allen et al. |
| 2003/0224019 A1 | 12/2003 | O'Brien |

(Continued)

FOREIGN PATENT DOCUMENTS

| | | |
|---|---|---|
| JP | 2005154321 A | 12/2006 |
| KR | 20080052510 A | 6/2008 |

(Continued)

OTHER PUBLICATIONS

Widera et al, "Effect of delivery parameters on immunization to ovalbumin following intracutaneous administration by a coated microneedle array patch system", Vaccine, 24:1653-1664 (2006).
Lin et al "Silicon-Processed Microneedles", IEEE Journal of Microelectromechanical Systems, 8(1):78-84 (1999).
Sullivan et al, "Minimally invasive protein delivery with rapidly dissolving polymer microneedles", Adv Mater. 20(5):933-938 (2008).
Goldman, "Treatment of axillary and palmar hyderhidrosis with botulinum toxin", Aesthetic Plast. Surg., 4:280-2 (2000) Abstract Only.
Childers et al, "Botulinum toxin type A use in piriformis muscle syndrome: a pilot study", Am J Phys Med Rehabil., 81(10)751-9 (2002) Abstract Only.

(Continued)

*Primary Examiner* — Padmavathi Baskar
(74) *Attorney, Agent, or Firm* — DLA Piper LLP

(57) ABSTRACT

The present invention relates to microstructure formulation techniques for botulinum toxin. The microstructure formulation techniques for botulinum toxin according to the present invention make it possible to precisely control the concentration of botulinum toxin and to alleviate the pain occurring when botulinum toxin is administered into the human body, and also enable botulinum toxin to be accurately administered to a desired position. Thus, the present invention is expected to greatly contribute to the safe and convenient medical use of botulinum toxin.

2 Claims, 6 Drawing Sheets
(6 of 6 Drawing Sheet(s) Filed in Color)

(56) References Cited

U.S. PATENT DOCUMENTS

| | | |
|---|---|---|
| 2004/0009180 A1 | 1/2004 | Donovan |
| 2008/0015421 A1 | 1/2008 | Penner |
| 2008/0113051 A1 | 5/2008 | Hunt |

FOREIGN PATENT DOCUMENTS

| | | |
|---|---|---|
| WO | 9633273 A1 | 1/1996 |
| WO | 9807864 A1 | 2/1998 |
| WO | 9917806 A1 | 4/1999 |
| WO | 0010598 A2 | 3/2000 |
| WO | 0057897 A1 | 10/2000 |
| WO | 0121213 A2 | 3/2001 |
| WO | 03011333 A1 | 2/2003 |
| WO | 2007041664 A1 | 4/2007 |
| WO | 2009105369 A1 | 8/2009 |
| WO | 201253266 A2 | 11/2012 |
| WO | 2012153266 A3 | 11/2012 |
| WO | 2013153550 A3 | 10/2013 |
| WO | 2015020982 A2 | 2/2015 |
| WO | 2015020982 A3 | 2/2015 |

OTHER PUBLICATIONS

Blugerman et al, "Mutiple eccrine hidrocystomas: a new therapeutic option with botulinum toxin", Dermatol Surg., 29(5):557-9 (2003) Abstract Only.

Jost, "Ten years' experience with botulin toxin in anal fissure", Int J Colorectal Dis., 17(5):298-302, Epub 2002, Abstract Only.

Heckmann et al, "Botulinum toxin type A injection in the treatment of lichen simplex: an open pilot study", J Am Acad Dermatol., 46(4):617-9 (2002) Abstract Only.

Li et al, "Sensory and motor denervation influence epidermal thickness in rat foot glabrous skin", Exp Neurol., 147(2):452-62 (1997) Abstract Only.

Katsambas et al, "Cutaneous Diseases of the Foot: Unapproved Treatments", Clin Dermatol, 20(6):689-699 (2002) First page only.

Sevim et al, "Botulinum toxin—A therapy for palmar and plantar hyperhidrosis", Acta Neurol Belg., 102(4):167-70 (2002) Abstract Only.

Suputitada, "Local botulinum toxin type A injections in the treatment of spastic toes", Am J Phys Med Rehabil, 81(10):770-5 (2002) Abstract Only.

Park et al, "Polymer microneedles for controlled-release drug delivery", Pharm Res., 23(5):1008-19 (2006) Abstract Only.

Dabrowski et al, "Botulinum toxin as A novel treatment for self-mutilation in Lesch-Nyhan syndrome", Dev Med Child Neurol., 47(9):636-9 (2005) Abstract Only.

Park et al, "Biodegradable polymer microneedles: fabrication, mechanics and transdermal drug delivery", J Control Release, 104(1):51-66 (2005) Abstract Only.

Torrisi, "Liquid loaded microneedles for the intradermal delivery of botulinum toxin for Primary Focal Hyperhidrosis", Doctoral Thesis, Cardiff School of Pharmacy and Pharmaceutical Science (2012).

Torrisi et al, "Pocketed microneedles for rapid delivery of a liquid-state botulinum toxin A formulation into human skin," Journal of Controlled Release, 165:146-152 (2013).

Kim et al, "Microneedles for drug arid vaccine delivery", Drug Delivery Reviews, 64:1547-1568 (2012).

【Figure 1】
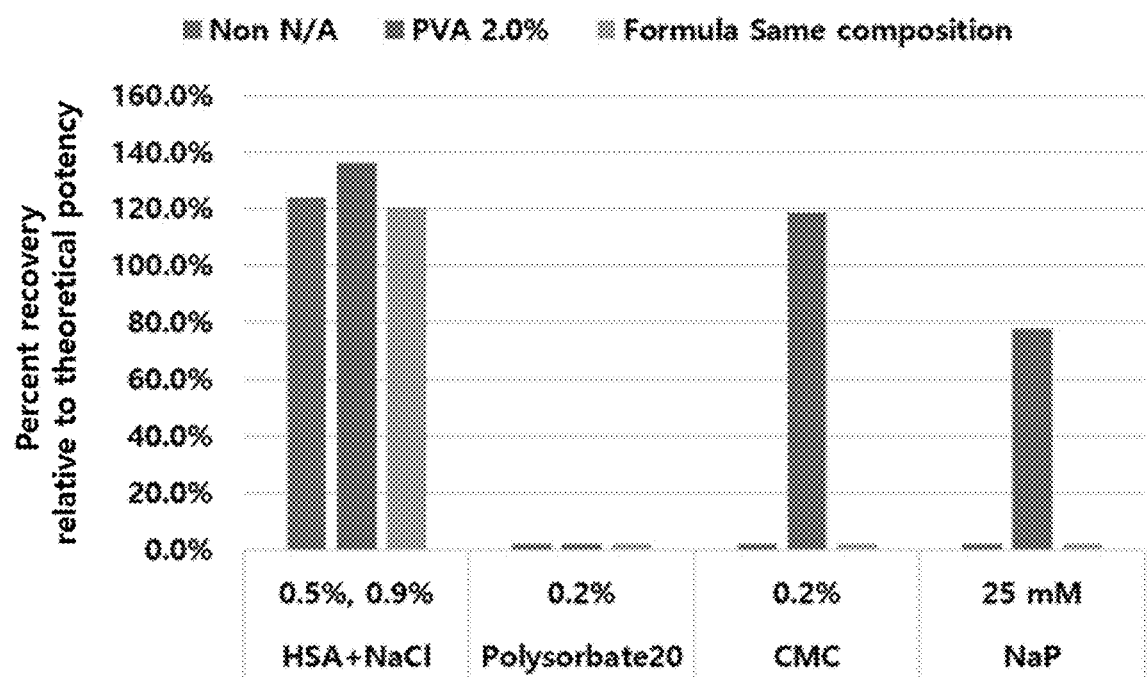

[Figure 2]
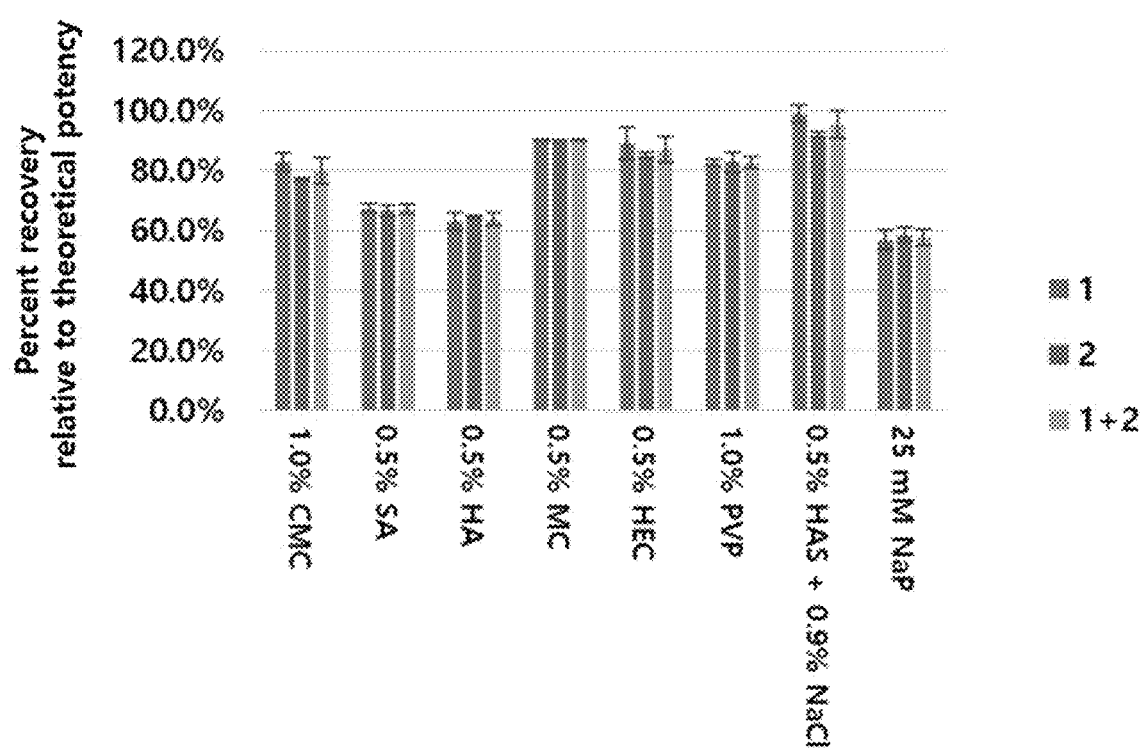

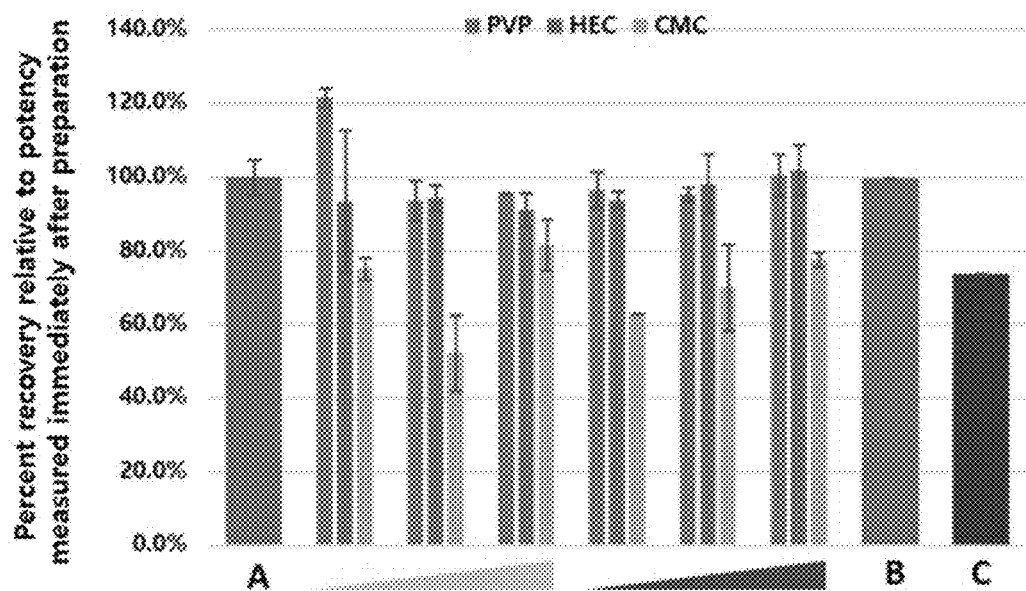
[Figure 3]

[Figure 4]
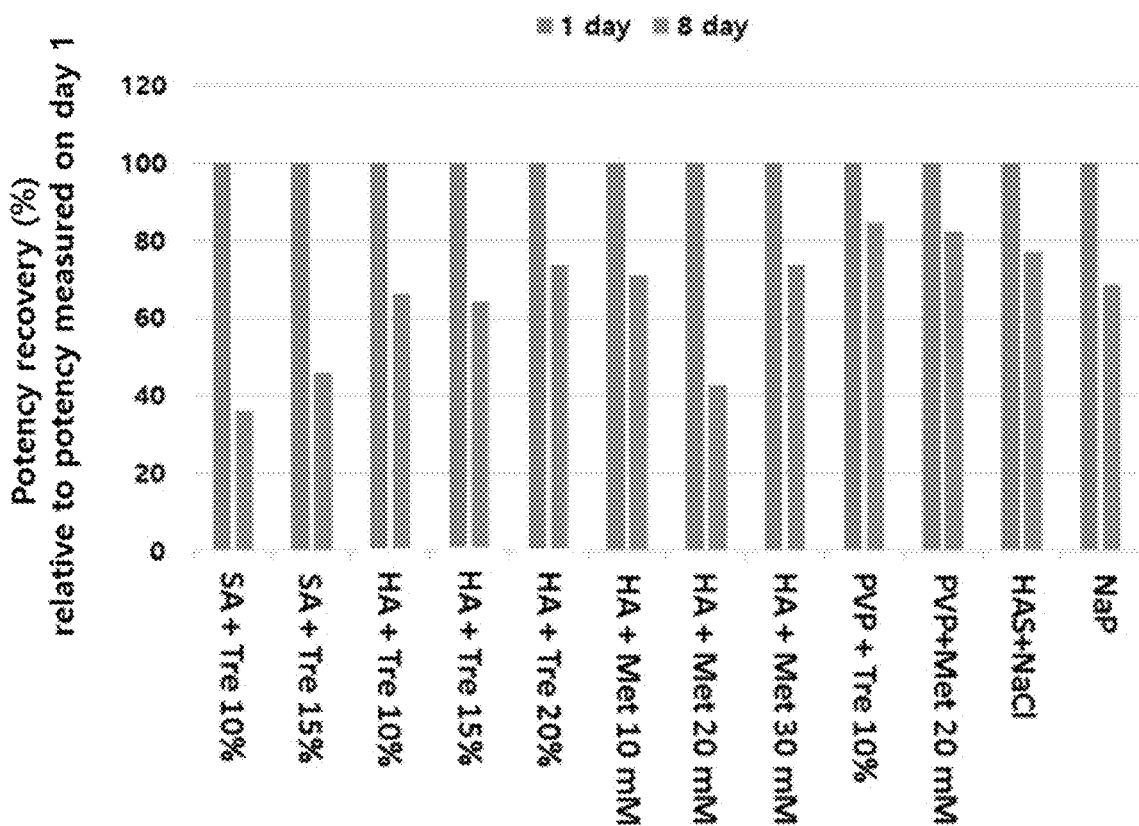

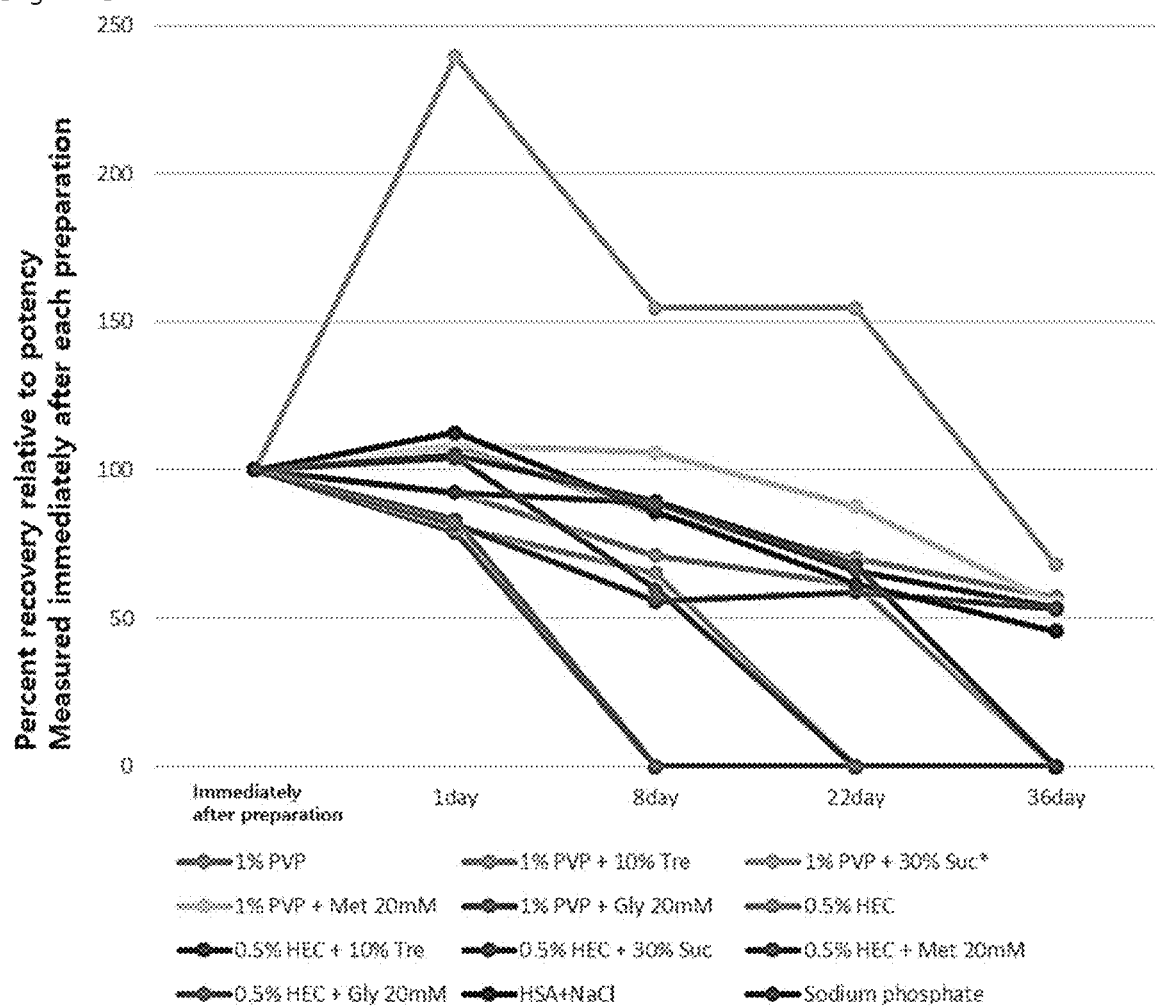
[Figure 5]

[Figure 6]
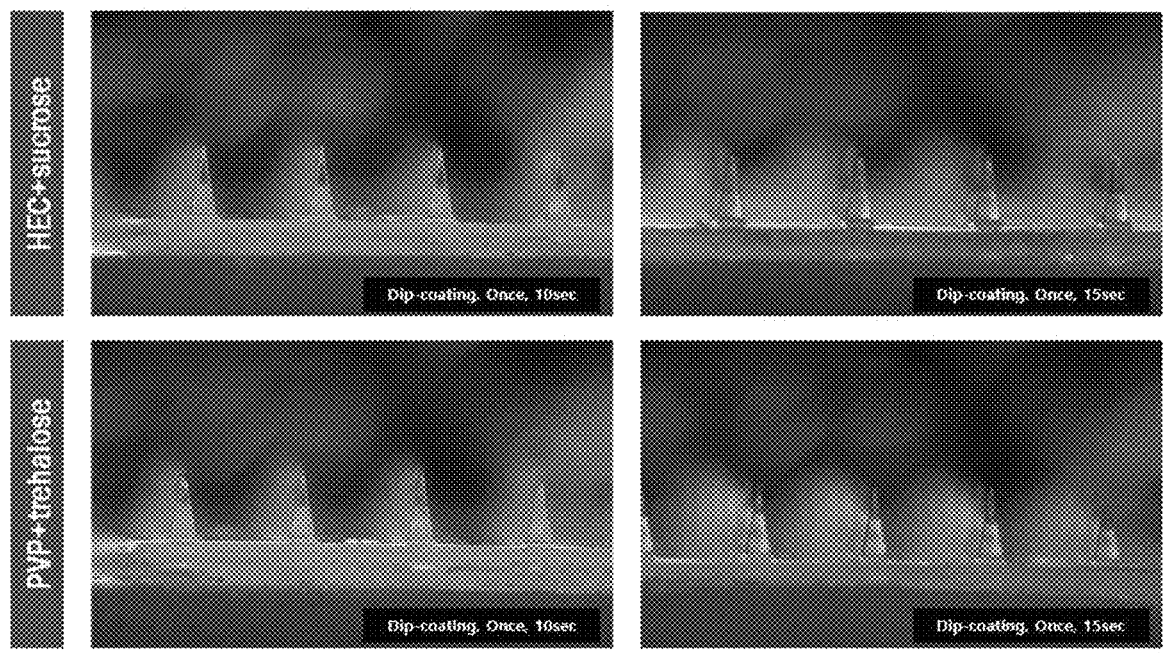

MICROSTRUCTURE FORMULATION TECHNIQUES FOR BOTULINUM TOXIN

This application is a continuation in part of U.S. patent application Ser. No. 15/730,969, filed Oct. 12, 2017, and the entirety of which is incorporated by reference herewith.

TECHNICAL FIELD

Technical Field

The present invention relates to microstructure formulation techniques for botulinum toxin.

Background Art

A variety of *Clostridium* sp. strains which secrete toxins having neurotoxic effects have been discovered since the 1890s up to the present time, and the characterization of toxins that are secreted from these strains has been made during the past 70 years (Schant, E. J. et al., Microbiol. Rev., 56:80, 1992). Among these toxins, botulinum toxin is classified into seven subtypes (subtypes A to G) according to their serological characteristics, and inhibits the exocytosis of acetylcholine at the cholinergic presynapse of a neuromuscular junction in animals having neurological function to thereby cause asthenia universalis. It is known that subtypes B, D, F and G of botulinum toxin cleave synaptobrevin at a specific site, subtypes A and E cleave SNAP25 at a specific site, and subtype C cleaves syntaxin at a specific site (Binz, T. et al., J. Biol. Chem., 265:9153, 1994). Thus, efforts have recently been made to use the neurotoxicity of botulinum toxin for cosmetic or therapeutic purposes. Technologies for using botulinum toxin for treatment of optic diseases (U.S. Pat. No. 6,265,379), pain (U.S. Pat. No. 6,113,915), various autonomic nerve disorders, including sweat gland disorders (U.S. Pat. No. 5,766,605), migraine headache (U.S. Pat. No. 5,714,468), post-operative pain and visceral pain (U.S. Pat. No. 6,464,986), psoriasis and dermatitis (U.S. Pat. No. 5,670,484), various cancers (U.S. Pat. Nos. 6,139,845 and 6,063,768), and neurogenic inflammation (U.S. Pat. No. 6,063,768), have been proposed or attempted.

However, botulinum toxin is the most lethal substance among known biological toxins, with an estimated human median lethal dose (LD50) of 1.3-2.1 ng/kg intravenously or intramuscularly, and 10-13 ng/kg when inhaled. As described above, botulinum toxin has great therapeutic effects on various diseases, but is lethal even in a very small amount due to its strong toxicity. For this reason, when botulinum toxin is to be used in a living body, it is necessary to precisely control the concentration of botulinum toxin.

Meanwhile, microstructures include microneedles, microblades, microknifes, microfibers, microspikes, microprobes, microbarbs, microarrays or microelectrodes, and among them, the term "microneedle" means a technology that forms a hole through the skin by use of a fine needle to increase drug penetration. In particular, when microneedles are used to deliver botulinum toxin, the toxin is injected with several tens to hundreds of microneedles, and thus pain caused by the injection can be alleviated and side effects resulting from a failure to accurately administer the toxin to a desired position can be avoided.

Thus, in this case, there is an advantage in that the drug release rate can be controlled depending on the choice of the material and a preparation method for the microneedle. When the microstructures of the present invention are used to administer botulinum toxin, pain can be alleviated and trace amounts of the toxin can be accurately administered to a desired position. Thus, the microstructures of the present invention are expected to greatly contribute to the safe and convenient medical use of botulinum toxin.

DISCLOSURE

Technical Problem

The present invention has been made in order to solve the above-described problems occurring in the prior art, and it is an object of the present invention to provide microstructure formulation techniques for botulinum toxin.

However, the technical object to be achieved by the present invention is not limited to the above technical object, and other objects that are not mentioned above can be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise specified in the specification, all the scientific and technical terms used in the specification have the same meanings as commonly understood by those skilled in the technical field to which the present invention pertains.

In one embodiment of the present invention, "botulinum toxin" is a neurotoxic protein produced by the bacterium *Clostridium botulinum*. The genus *Clostridium* has more than 127 species, grouped according to their morphology and functions. The anaerobic, gram-positive bacteria *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The symptoms of botulism typically appear 18 to 36 hours after eating the foodstuffs infected with a *Clostridium botulinum* culture or spores. The botulinum toxin can apparently pass unattenuated through the lining of the gut and shows a high affinity for cholinergic motor neurons. Symptoms of botulinum toxin intoxication can progress from difficulty in walking, swallowing, and speaking to paralysis of the respiratory muscles and death. Botulinum toxin type A is known as the most lethal natural biological agent to man. About 50 picograms of a commercially available botulinum toxin type A (purified neurotoxin complex) is an LD50 (i.e., 1unit). Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. One unit (U) of botulinum toxin is defined as the LD50 upon intraperitoneal injection into female Swiss Webster mice weighing 18 to 20 grams each.

Immunologically distinct 7 botulinum neurotoxins have been generally characterized as botulinum neurotoxin serotypes A, B, C1, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than botulinum toxin type B. Additionally, botulinum toxin type B has been determined to be non-toxic in primates at a dose of 480 U/kg which is about 12 times the primate LD50 for botulinum toxin type A. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least 3 steps. In the first step of the process, the toxin binds to the presynaptic membrane of the target neuron through a specific interaction between the heavy chain (the H chain or HC), and a cell surface receptor. The receptor is thought to be different for each type of botulinum toxin and for tetanus toxin. The carboxyl end segment of the HC appears to be important for targeting of the botulinum toxin to the cell surface.

In the second step, the botulinum toxin crosses the plasma membrane of the target cell. The botulinum toxin is first engulfed by the cell through receptor-mediated endocytosis, and an endosome containing the botulinum toxin is formed. The toxin then escapes the endosome into the cytoplasm of the cell. This step is thought to be mediated by the amino end segment of the heavy chain, the HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the botulinum toxin to embed itself in the endosomal membrane. The botulinum toxin (or at least the light chain of the botulinum toxin) then translocates through the endosomal membrane into the cytoplasm.

The last step of the mechanism of botulinum toxin activity appears to involve reduction of the disulfide bond joining the heavy chain and the light chain. The entire toxic activity of botulinum and tetanus toxins is contained in the light chain of the holotoxin; the light chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype C1 was originally thought to cleave syntaxin, but was found to cleave syntaxin and SNAP-25. Each of the botulinum toxins specifically cleaves a different bond, except type B (and tetanus toxin) which cleave the same bond. Each of these cleavages blocks the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989, a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about 3 months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and cleaving these proteins at different sites. For example, botulinum types A and E both cleave the 25 kDa synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 appears to cleave both syntaxin and SNAP-25. These differences in mechanism of action may affect the relative potency and/or duration of action of the various botulinum toxin serotypes. Particularly, a substrate for a botulinum toxin can be found in a variety of different cell types.

The molecular weight of the botulinum toxin, for all seven of the known botulinum toxin serotypes, is about 150 kDa. Interestingly, the botulinum toxins are released by Clostridial bacterium as complexes comprising the 150 kDa botulinum toxin protein molecule along with associated non-toxin proteins. Thus, the botulinum toxin type A complex can be produced by Clostridial bacterium as 900 kDa, 500 kDa or 300 kDa forms. Botulinum toxin types B and C1 are apparently produced as only a 700 kDa or 500 kDa complex. Botulinum toxin type D is produced as 300 kDa or 500 kDa complexes. Finally, botulinum toxin types E and F are produced as only approximately 300 kDa complexes. The complexes (i.e. molecular weight greater than about 150 kDa) are believed to contain a non-toxin hemagglutinin proteins, a non-toxin, and non-toxic non-hemagglutinin protein. These two non-toxin proteins (which along with the botulinum toxin molecule comprise the relevant neurotoxin complex) may act to provide stability against denaturation to the botulinum toxin molecule and protection against digestive acids when a botulinum toxin is ingested. Additionally, it is possible that the larger (greater than about 150 kDa molecular weight) botulinum toxin complexes result in a slower rate of diffusion of the botulinum toxin away from a site of intramuscular injection of a botulinum toxin complex.

In vitro studies have indicated that botulinum toxin inhibits potassium cation-induced release of both acetylcholine and norepinephrine from primary cell cultures of brainstem tissue. In addition, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP substance P, and glutamate. Thus, when adequate concentrations are used, the stimulus-evoked release of most neurotransmitters can be blocked by botulinum toxin.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can, therefore, be recovered from bacterial cultures in predominantly their active form. In contrast, botulinum toxin serotypes C1, D, and E are synthesized by nonproteolytic strains and are therefore typically inactivated when recovered from culture. Serotypes B and F are produced by both proteolytic and nonproteolytic strains, and thus can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Moreover, it is known that botulinum toxin type B has, upon intramuscular injection, a shorter duration of activity and is also less potent than botulinum toxin type A at the same dose level.

High-quality crystalline botulinum toxin type A can be produced from the Hall A strain of *Clostridium botulinum* with characteristics of $\geq 0.3 \times 10^7$ U/mg, an A260/A278 of less than 0.60 and a distinct pattern of banding on gel electrophoresis. The known Schantz process can be used to obtain crystalline botulinum toxin type A. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kDa molecular weight with a specific potency of $1-2 \times 10^8$ LD50 U/mg or greater; purified botulinum toxin type B with an approximately 156 kDa molecular weight with a specific potency of $1-2 \times 10^8$ LD50 U/mg or greater, and; purified botulinum toxin type F with an approximately 155 kDa molecular weight with a specific potency of $1-2 \times 10^7$ LD50 U/mg or greater.

Botulinum toxins and/or botulinum toxin complexes are commercially available from compound manufacturers known in the art, and pure botulinum toxin can also be used to prepare a pharmaceutical composition.

As with enzymes generally, the biological activities of the botulinum toxins (which are intracellular peptidases) are dependent, at least in part, upon their three dimensional conformation. Thus, botulinum toxin type A is detoxified by heat, various chemicals surface stretching and surface drying. Additionally, it is known that dilution of a botulinum toxin complex obtained by the known culturing, fermentation and purification to the very low toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the toxin containing pharmaceutical composition is formulated, the toxin should be stabilized with a suitable stabilizing agent. Thus, as disclosed in the present invention, the development of optimal stabilizer technology is necessary to control the in vivo release of botulinum toxin to a slow release form.

It has been reported that botulinum toxin type A has been used in clinical settings as follows: The usual duration of an intramuscular injection of botulinum toxin administered in vivo is typically about 3 to 4 months. However, in some cases, botulinum toxin subtype A can have an efficacy for up to 12 months (*European J. Neurology* 6 (Supp 4): S111-S1150:1999), and in some circumstances for as long as 27 months, when used to treat glands, such as in the treatment of hyperhydrosis.

In addition to having pharmacologic actions at the peripheral location, botulinum toxins may also have inhibitory effects in the central nervous system. Work by Weigand et al, *Naunny-Schmiedeberg's Arch. Pharmacol.* 1976; 292, 161-165, and Habermann, *Naunny-Schmiedeberg's Arch. Pharmacol* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

A botulinum toxin has also been proposed for or has been used to treat skin bone and tendon wounds (U.S. Pat. No. 6,447,787); intrathecal pain (see U.S. Pat. No. 6,113,915); various autonomic nerve disorders, including sweat gland disorders (see e.g. U.S. Pat. No. 5,766,605 and Goldman (2000), Aesthetic Plastic Surgery July-August 24(4):280-282); tension headache (U.S. Pat. No. 6,458,365); migraine headache (U.S. Pat. No. 5,714,468); post-operative pain and visceral pain (U.S. Pat. No. 6,464,986); hair growth and hair retention (U.S. Pat. No. 6,299,893); psoriasis and dermatitis (U.S. Pat. No. 5,670,484); injured muscles (U.S. Pat. No. 6,423,319); various cancers (U.S. Pat. Nos. 6,139,845 and 6,063,768), smooth muscle disorders (U.S. Pat. No. 5,437,291); nerve entrapment syndromes (US Patent Application 2003-0224019); acne (WO 03/011333); neurogenic inflammation (U.S. Pat. No. 6,063,768); optic disorders (see U.S. Pat. No. 6,265,379); pancreatic disorders (see U.S. Pat. Nos. 6,143,306 and 6,261,572); prostate disorders, including prostatic hyperplasia, prostate cancer and urinary incontinence (see U.S. Pat. Nos. 6,365,164 and 6,667,041 and Doggweiler R., et al *Botulinum* toxin *type A causes diffuse* and *highly selective atrophy of rat prostate*, Neurourol Urodyn 1998; 17(4):363); fibromyalgia (U.S. Pat. No. 6,623,742), and *piriformis* muscle syndrome (see Childers et al. (2002), American Journal of Physical Medicine & Rehabilitation, 81:751-759).

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord. Additionally, it has been disclosed that targeted botulinum toxins (i.e. with a non-native binding moiety) can be used to treat various conditions (see WO 96/33273; WO 99/17806; WO 98/07864; WO 00/57897; WO 01/21213; WO 00/10598).

In addition, a botulinum toxin has been injected into the pectoral muscle to control pectoral spasm (Senior M., Botox and the management of pectoral spasm after subpectoral implant insertion, Plastic and Recon Surg, July 2000, 224-225). Controlled release toxin implants are known (see U.S. Pat. Nos. 6,306,423 and 6,312,708) as is transdermal botulinum toxin administration (U.S. patent application Ser. No. 10/194,805). It is known that a botulinum toxin can be used to: weaken the chewing or biting muscle of the mouth so that self inflicted wounds and resulting ulcers can be healed (Payne M., et al, Botulinum toxin as a novel treatment for self mutilation in Lesch-Nyhan syndrome, Ann Neurol 2002 September; 52 (3 Supp 1):5157); permit healing of benign cystic lesions or tumors (Blugerman G., et al., Multiple eccrine hidrocystomas: A new therapeutic option with botulinum toxin, Dermatol Surg 2003 May; 29(5):557-9); treat anal fissure (Jost W, Ten years' experience with botulinum toxin in anal fissure, Int J Colorectal Dis 2002 September; 17(5):298-302); and treat certain types of atopic dermatitis (Heckmann M., et al., Botulinum toxin type A injection in the treatment of lichen simplex: An open pilot study, J Am Acad Dermatol 2002 April; 46(4):617-9).

Additionally, a botulinum toxin may have the effect of reducing induced inflammatory pain in a rat formalin model (Aoki K, et al, Mechanisms of the antinociceptive effect of subcutaneous Botox: Inhibition of peripheral and central nociceptive processing, Cephalalgia 2003 September; 23(7): 649). Furthermore, it has been reported that botulinum toxin nerve blockage can cause a reduction of epidermal thickness (Li Y, et al., Sensory and motor denervation influences epidermal thickness in rat foot glabrous skin, Exp Neurol 1997; 147:452-462). Finally, it is known to administer a botulinum toxin to the foot to treat excessive foot sweating (Katsambas A., et al., Cutaneous diseases of the foot: Unapproved treatments, Clin Dermatol 2002 November-December; 20(6):689-699; Sevim, S., et al., Botulinum toxin-A therapy for palmar and plantar hyperhidrosis, Acta Neurol Belg 2002 December; 102(4):167-70), spastic toes (Suputtitada, A., Local botulinum toxin type A injections in the treatment of spastic toes, Am J Phys Med Rehabil 2002 October; 81(10):770-5), idiopathic toe walking (Tacks, L., et al., Idiopathic toe walking: Treatment with botulinum toxin A injection, Dev Med Child Neurol 2002; 44(Suppl 91):6), and foot dystonia (Rogers J., et al., Injections of botulinum toxin A in foot dystonia, Neurology 1993 April; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight: about 50 kDa) covalently bound by a single disulfide bond to a heavy chain (molecular weight: about 100 kDa). Hence, the molecular weight of tetanus toxin and of each of the 7 botulinum toxins (non-complexed) is about 150 kDa. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor-mediated endocytosis of tetanus toxin in peripheral cholinergic neurons results in retrograde axonal transport, blocking the release of inhibitory neurotransmitters from central synapses, and causing a spastic paralysis. Contrarily, it has been believed that receptor-mediated endocytosis of botulinum toxin in peripheral cholinergic neuronshardly results in retrograde transport, inhibition of acetylcholine exocytosis from the central synapses, and a flaccid paralysis. However, very recent report has suggested that botulinum toxin also can undergo retrograde transport along axons and possibly inhibit the release of acetylcholine in central synapse (Bomba-Warczak et al., Interneuronal Transfer and Distal Action of Tetanus Toxin and Botulinum Neurotoxins A and D in Central Neurons, Cell Reports, 2016 August; 16, 1974-1987).

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains (Binz T. et al., The Complete Sequence of Botulinum Neurotoxin Type A and Comparison with Other Clostridial Neurotoxins, J Biological Chemistry 265 (16); 9153-9158:1990).

In one embodiment of the present invention, "acetylcholine" is an ester of choline and acetic acid, which is the first known neurotransmitter. It is distributed throughout neurons, and has a chemical formula of $C_7H_{16}NO_2$ and a molecular weight of 146.21 kDa.

Typically, only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, specifically by the large pyramidal cells of the motor cortex, several different neurons in the basal ganglia, the motor neurons that innervate the skeletal muscles, the preganglionic neurons of the autonomic nervous system (both sympathetic and parasympathetic), the bag 1 fibers of the muscle spindle fiber, the postganglionic neurons of the parasympathetic nervous system, and some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances, acetylcholine has an excitatory effect. However, acetylcholine is known to have inhibitory effects at some of the peripheral parasympathetic nerve endings (for example, inhibition of heart rate by the vagal nerve).

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, when the denervated cells are permeabilized (as by electroporation) or directly injected with the toxin. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

In one embodiment of the present invention, "microstructures" include microneedles, microblades, microknifes, microfibers, microspikes, microprobes, microbarbs, microarrays or microelectrodes, but are not limited thereto. Particularly, the microstructures that are used in the present invention are preferably microneedles. In addition, when microneedles that are used in medical applications as disclosed in the present invention are manufactured, these microneedles are preferably made of a "biocompatible or biodegradable material". As used herein, the term "biocompatible material" refers to a material that is non-toxic to the human body and is chemically inactive. In addition, the term "biodegradable material" refers to a material that can be degraded in vivo by body fluids, enzymes or microorganisms. As used herein, the term "microstructure" refers to either one manufactured to include therein a botulinum toxin composition of the present invention, which contains a botulinum toxin, a thickener and a stabilizer as active ingredients, or one coated with the botulinum toxin composition of the present invention. The microstructures that are used in the present invention include any microstructures manufactured by the microstructure manufacturing methods used in the art, and are not limited by the manufacturing methods.

In one embodiment of the present invention, the term "microneedle" refers to a technology that forms a hole in the skin by use of a microneedle to increase drug penetration. The microneedles are mainly used for in vivo drug delivery, blood collection, in vivo analyte detection, etc.

In 1998, the Georgia Institute of Technology (USA) made a microstructure array as a silicon device by use of semiconductor process technology, and first suggested the potential of the microstructure array as a technology that replaces subcutaneous injection.

Unlike conventional needles, microneedles should not cause pain when they penetrate the skin, and for such painless skin penetration, the diameter of the top for the minimum sharpness is important. In addition, the microneedle should have a physical hardness sufficient to penetrate a 10-20 μm thick stratum corneum that is the strongest barrier in the skin. Furthermore, the microneedle should have a suitable length so as to reach capillaries to thereby increase the efficiency of drug delivery.

Since in-plane microneedles were suggested (Silicon-processed Microneedles, Journal of microelectrochemical systems 8, 1999), various types of microneedles have been developed. For example, a solid silicon microneedle array made using an etching method was suggested as an out-of-plane microneedle array (US Patent Publication No. 2002138049). The solid silicon microneedle according to this method has a diameter of 50-100 μm and a length of 500 μm, but it is impossible to realize painless skin penetration, and in vivo delivery of a drug or a cosmetic component to the target site is not reliably achieved. Meanwhile, Prausnitz (University of Georgia, USA) suggested a method of making biodegradable polymer microneedles, which comprises preparing a mold by etching of glass or by photolithography (Biodegradable polymer microneedles: Fabrication, mechanics and transdermal drug delivery, Journal of Controlled Release 104, 2005, 5166). Furthermore, in 2006, a method of making biodegradable microneedles by loading a capsule-type material onto the end of a mold made by a photolithography method was proposed (Polymer Microneedles for Controlled-Release Drug Delivery, Pharmaceutical Research 23, 2006, 1008). The use of this method has an advantage in that a capsule-type drug is easily loaded. However, as the amount of drug loaded increases, the hardness of the microneedles decreases, indicating that the application of this method to a drug that needs to be administered in large amounts is limited.

In 2005, an absorption type microneedle was suggested by Nano Device and Systems Inc. (Japanese Unexamined Patent Application Publication No. 2005154321). This absorption type microneedle is to be used in drug delivery or cosmetic care without removing the microneedle inserted into the skin. In this method, a microneedle was made by applying a composition containing maltose to a mold and solidifying the composition. The above-described Japanese patent publication suggests transdermal absorption of a drug through the absorption-type microneedle, but the microneedle caused pain when penetrating the skin. In addition, due to a technical limitation in mold making, it was impossible to make a microneedle that has a proper top diameter causing no pain and a length in the range required for effective drug delivery, i.e. a length equal to or greater than 1 mm.

A biodegradable microneedle suggested by Prausnitz (Georgia University, USA.) in 2008 was made with a polydimethylsiloxane (PDMS) mold and a mixture of polyvinylpyrrolidone (PVP) and methacrylic acid (MAA) (Minimally Invasive Protein Delivery with Rapidly Dissolving Polymer Microneedles, Advanced Materials 2008, 1). Further, a microneedle was made by placing carboxymethylcellulose in a pyramidal mold (Dissolving microneedles for transdermal drug delivery, Biomaterials 2007, 1). However, the making method using the mold has a limitation in that a new template and mold need to be made through a complicated process to control the diameter and length of a microneedle. In addition, it has disadvantages in that a process of manufacturing a microneedle by placing a material in a mold is complicated and is time-consuming.

In 2008, Mukai et al. (Japan) disclosed an apparatus and method of manufacturing a skin needle using a pin structure (US Patent Publication No. 20080157421A1). This method includes heating a viscous material on a base of a substrate and pulling the viscous material using tensile force by means of a pin. Because the method involves pulling a material, which is melted by heat or is viscous, using a pin structure, it further requires a process of making a new pin structure according to a desired pattern, resulting in an increased production cost, and the heating process makes it difficult to load various heat-sensitive biodrugs (hormones, vaccines, other protein drugs, etc.).

The skin is composed of stratum corneum (<20 μm), epidermis (<100 μm), and dermis (300-2,500 μm), which are sequentially stacked from the outer layer of the skin. Therefore, to deliver a drug and a physiologically active substance to a specific skin layer without causing pain, making a microneedle to have a top diameter of 30 μm or less, an effective length of 200-2,000 μm and a hardness sufficient for skin penetration is effective in delivering the drug and the skin care component. In addition, to deliver a drug or a physiologically active substance through a biodegradable solid microneedle, any process that may destroy the activity of the drug and the physiologically active substance, such as high-temperature treatment, organic solvent treatment, etc., should be eliminated from the microneedle making process.

Conventional solid microneedles are made using limited materials such as silicon, polymers, metals, glass, etc., due to a limit of the production method. Also, the use of the production method based on a molding technique causes a complicated and time-consuming process, which has disadvantages such as drug degeneration, insufficient hardness and the loss of drugs. Accordingly, there is an ongoing demand for a method for making a microneedle which has a thin diameter enabling painless skin penetration and a sufficient length enabling deep skin penetration and has a sufficient hardness regardless of the kind of material and also can minimize the loss of drugs.

In one embodiment of the present invention, the term "pharmaceutical composition" refers to a composition that is administered for a specific purpose. For the purpose of the present invention, the pharmaceutical composition of the present invention is configured such that the botulinum toxin can be accurately administered to a desired position at a precisely controlled concentration, and the pharmaceutical composition may include a protein and a pharmaceutically acceptable carrier, excipient or diluent, which are involved in this administration. The "pharmaceutically acceptable" carrier or excipient means the one approved by a regulatory agency of a government or listed in the Pharmacopeia or other generally recognized pharmacopeia for use in mammals, and more particularly in humans.

Microstructures containing a botulinum toxin as an active ingredient, which are suitable for parenteral administration, may be in the form of suspensions, solutions or emulsions in oily or aqueous carriers, or be prepared in the form of solid or semi-solid, and may contain formulating agents such as suspending agents, stabilizers, solubilizing agents and/or dispersing agents. This form may be sterilized and may be fluid. It can be stable under the conditions of manufacture and storage, and can be preserved against the contamination with microorganisms such as bacteria or fungi. Alternatively, microstructures containing a botulinum toxin as an active ingredient may be in the form of sterile powder for reconstitution with suitable carriers before use. Pharmaceutical compositions may be present in unit-dose form, microneedle patches, in ampoules, or other unit-dose containers or in multi-dose containers. Alternatively, the pharmaceutical compositions can be stored in a freeze-dried (lyophilized) condition requiring only the addition of sterile liquid carrier, for example, saline for injections, immediately prior to use. Extemporaneous injection solutions and suspensions can be prepared from sterile powders, granules or tablets.

In some non-limiting embodiments, microspheres containing a botulinum toxin as an active ingredient may be formulated as liquid, or may be contained in the form of microspheres in liquid. In any non-limiting embodiments, a microstructure liquid composition containing a botulinum toxin as an active ingredient contains a botulinum toxin or a pharmaceutically acceptable compound and/or mixture at a concentration of 0.001-100,000 U/kg. In any non-limiting embodiment, Excipients suitable for microsphere compositions containing a botulinum toxin as an active ingredient include preservatives, suspending agents, stabilizers, dyes, buffers, antibacterial agents, antifungal agents, and isotonic agents, for example, sugars or sodium chloride. As used herein, the term "stabilizer" refers to a compound optionally used in the pharmaceutical compositions of the present invention in order to increase storage life. In non-limiting embodiments, stabilizers may be sugars, amino acids, compounds or polymers, which sugars may be monosaccharides, disaccharides or polysaccharides, but is preferably disaccharides. The disaccharides are classified into reducing disaccharides and non-reducing disaccharides. Either monosaccharide of reducing disaccharide has a free hemiacetal unit that can act as reducing aldehydes. Cellobiose (Cel) and maltose (Mal) are examples of reducing disaccharides having one hemiacetal unit. On the other hand, non-reducing disaccharides lack hemiacetals that can function as reducing agents, because it is produced through the bond between the anomeric carbons of the two monosaccharides to form acetals. Trehalose (Tre) and Sucrose (Suc) are examples of non-reducing disaccharides. The pharmaceutical composition may contain one or more pharmaceutically acceptable carriers. The carrier can be a solvent or dispersion medium. Non-limiting examples of pharmaceutically acceptable carriers include water, ethanol, polyol (e.g., glycerol, propylene glycol and liquid polyethylene glycol), oils, and suitable mixtures thereof.

The parenteral formulation can be sterilized. Non-limiting examples of sterilization techniques include filtration through a bacterial-retaining filter, terminal sterilization, incorporation of sterilizing agents, irradiation, heating, vacuum drying, and freeze drying.

In one embodiment of the present invention, the term "administration" means introducing the composition of the present invention into a patient by any suitable method. The composition of the present invention may be administered via any general route, as long as it can reach a target tissue. The composition can be administered orally, intraperitoneally, intravenously, intramuscularly, subcutaneously, intracutaneously, intranasally, intrapulmonarily, intrarectally, or intrathecally. However, microstructures containing a botulinum toxin as an active ingredient according to the present invention are preferably administered intracutaneously using microneedles.

The treatment method according to the present invention may comprise administering a pharmaceutically effective amount of the pharmaceutical composition. In the present invention, the effective amount can vary depending on various factors, including the kind of disease, the severity of the disease, the kinds and contents of active ingredient and other ingredients contained in the composition, the kind of formulation, the patient's age, weight, general health state, sex and diet, administration time, the route of administration, the secretion rate of the composition, the period of treatment, and drugs used concurrently.

In one embodiment, the present invention provides a botulinum toxin composition containing, as active ingredient, a botulinum toxin, a thickener and a stabilizer. In the botulinum toxin composition of the present invention, the botulinum toxin may be any one or more selected from the group consisting of botulinum toxin type A, B, C, D, E, F, and G; the thickener may be any one or more selected from the group consisting of carboxymethyl cellulose sodium salt, sodium alginate, hyaluronic acid, methyl cellulose, hydroxyethyl cellulose, and polyvinyl pyrrolidone; the thickener may be contained in an amount of 0.05 to 10 wt %; the stabilizer may be any one or more selected from the group consisting of trehalose, sucrose, a combination of trehalose and sucrose, methionine, sodium phosphate, and a mixture of human serum albumin and sodium chloride; and the stabilizer may be contained in an amount of 0.03 to 50 wt %. In an embodiment, a mixture of trehalose and sucrose comprises about 5, 10, 20, 30, 40, 50, 60, 70, 80, 90, or 95% trehalose and about 95, 90, 80, 70, 60, 50, 40, 30, 20, 10, or 5% sucrose.

In another embodiment, the present invention provides a microstructure comprising the botulinum toxin composition. The microstructure may be any one or more selected from the group consisting of a microneedle, a microblade, a microknife, a microfiber, a microspike, a microprobe, a microbarb, a microarray, and a microelectrode.

In still another embodiment, the present invention provides a method for preparing a botulinum toxin composition, comprising a step of mixing a botulinum toxin, a thickener and a stabilizer. In the method of the present invention, the botulinum toxin composition may be any one or more selected from the group consisting of botulinum toxin type A, B, C, D, E, F, and G; the thickener may be any one or more selected from the group consisting of carboxymethyl cellulose sodium salt, sodium alginate, hyaluronic acid, methyl cellulose, hydroxyethyl cellulose, and polyvinyl pyrrolidone; the thickener may be mixed in an amount of 0.05 to 10 wt %; the stabilizer may be any one or more selected from the group consisting of trehalose, sucrose, a combination of trehalose and sucrose, methionine, sodium phosphate, and a mixture of human serum albumin and sodium chloride; and the stabilizer may be mixed in an amount of 0.03 to 50 wt %.

In yet another embodiment, the present invention provides a method for coating a target object with a botulinum toxin composition, the method comprising the steps of: (a) precoating the object with a polymer compound; (b) mixing a botulinum toxin, a thickener and a stabilizer to obtain a mixture; and (c) dipping the precoated object of step (a) into the mixture of step (b), followed by drying. In the coating method of the present invention, the polymer compound may be polyvinyl alcohol; the polyvinyl alcohol may be used in an amount of 0.5 to 10 wt %; the botulinum toxin may be botulinum toxin type A; the thickener may be any one or more selected from the group consisting of carboxymethyl cellulose sodium salt, sodium alginate, hyaluronic acid, methyl cellulose, hydroxyethyl cellulose, and polyvinyl pyrrolidone; the stabilizer may be any one or more selected from the group consisting of trehalose, sucrose, a combination of trehalose and sucrose, methionine, sodium phosphate, and a mixture of human serum albumin and sodium chloride; the target object may be a microstructure; and the microstructure may be a microneedle.

Hereinafter, each step of the present invention will be described in detail.

Advantageous Effects

Botulinum toxin inhibits the exocytosis of acetylcholine at the cholinergic presynapse of a neuromuscular junction in animals having neurological function to thereby cause asthenia. Botulinum toxin has great therapeutic effects on various diseases due to its neurotoxic function, but is lethal even in a very small amount due to its strong toxicity. For this reason, when botulinum toxin is to be used in a living body, it is necessary to precisely control the concentration of botulinum toxin. The present invention relates to microstructure formulation techniques for botulinum toxin. When the microstructures of the present invention are used to administer botulinum toxin, pain can be alleviated and trace amounts of the toxin can be accurately administered to a desired position. Thus, the microstructures of the present invention are expected to greatly contribute to the safe and convenient medical use of botulinum toxin.

DESCRIPTION OF DRAWINGS

The patent or application file contains at least one drawing executed in color. Copies of this patent application publication with color drawing(s) will be provided by the Office upon request and payment of the necessary fee.

FIG. 1 shows the results of measuring the percent recovery relative to the theoretical potency of botulinum toxin depending on the kind of precoating material in an example of the present invention.

FIG. 2 shows the results of measuring the percent recovery relative to the theoretical potency of botulinum toxin depending on the kind and concentration of thickener mixed with botulinum toxin, in an example of the present invention.

FIG. 3 shows the results of measuring the percent recovery relative to the theoretical potency of botulinum toxin depending on the kind and concentration of stabilizer mixed with the botulinum toxin, in an example of the present invention.

FIG. 4 shows the results of measuring the long-term stabilities of combinations of a SA or HA thickener and a stabilizer in an example of the present invention.

FIG. 5 shows the results of measuring the long-term stabilities of combinations of a PVP or HEC thickener and a stabilizer in an example of the present invention.

FIG. 6 shows the results of confirming the coating uniformity of the coating composition containing a botulinum toxin.

BEST MODE

The present invention is provided a coating composition, containing: a botulinum toxin; a thickener; and a stabilizer. In the coating composition, the botulinum toxin may be selected from the group consisting of botulinum toxin type A, B, C, D, E, F and G. The botulinum toxin is preferably botulinum toxin type A. The thickener may be any one or more selected from the group consisting of carboxymethylcellulose sodium salt, sodium alginate, hyaluronic acid, methyl cellulose, hydroxyethyl cellulose, and polyvinyl pyrrolidone, and the thickener may be contained in an amount of 0.05-10 wt %. The stabilizer may be any one or more selected from the group consisting of trehalose, methionine, sodium phosphate, and a mixture of human serum albumin and sodium chloride, and the stabilizer may be contained in an amount of 0.03-30 wt %. The coating composition may be coated on the surface of a microstructure, and the microstructure may be a microneedle, a microblade, a microknife, a microfiber, a microspike, a microprobe, a microbarb, a microarray or a microelectrode. The microstructure is preferably a microneedle.

Mode for Invention

Hereinafter, the present invention will be described in further detail with reference to examples. It will be obvious to those skilled in the art that these examples are for illustrative purposes only and are not intended to limit the scope of the present invention.

Example 1: Examination of Dilution Factor for Testing Botulinum Toxin Potency

Because the loss rate of botulinum toxin potency, which occurs when a 2× coating composition and a 2× botulinum toxin composition are mixed with each other, cannot be seen, a preliminary experiment was performed in order to examine the change in botulinum toxin potency immediately after preparation of a botulinum toxin composition.

For this, a 2× coating composition and a 2× botulinum toxin composition were prepared individually and mixed at a ratio of 1:1, thereby preparing mixture compositions as shown in Table 1 below.

TABLE 1

| Preparation Example | Final concentration after mixing of 2 × coating composition and 2 × botulinum toxin composition |
|---|---|
| HSA + NaCl | 0.5% HSA, 0.9% NaCl, 5000 U toxin/6.5 µl |
| Tween 20 | 0.2% Tween 20, 5000 U toxin/6.5 µl |
| CMC | 1% CMC, 5000 U toxin/6.5 µl |
| Sodium phosphate (pH 6.0) | 0.025M sodium phosphate, 5000 U toxin/6.5 µl |

HSA (human serum albumin)
NaCl (sodium chloride)
CMC (carboxymethylcellulose sodium salt)
Sodium phosphate For the above-described mixture compositions, the potency of botulinum toxin was measured using an in vitro potency measurement kit (BoTest® Matrix Botulinum Neurotoxin Detection Kits, Biosentinel, Inc.). Specifically, the measurement was performed in the same manner as described in Dunning F M et al., J Vis Exp. 2014 Mar. 3; (85). doi: 10.3791/51170. Furthermore, considering the case in which the potency would decrease immediately after preparation, two dilution factors (75 and 112.5) were applied. The results of the measurement are shown in Table 2 below.

TABLE 2

| Preparation Example | Theoretical potency (U/6.25 µl) | Dilution factor | Measured Potency (U) | Average potency | SD | RSD | Potency Recovery (%) |
|---|---|---|---|---|---|---|---|
| HSA + NaCl | 5000 | 75 | 6169.0 | 6240 | 100.7 | 1.6 | 124.8 |
|  |  | 112.5 | 6311.4 |  |  |  |  |
| Tween 20 | 5000 | 75 | 6465.4 | 6561 | 135.2 | 2.1 | 131.2 |
|  |  | 112.5 | 6656.7 |  |  |  |  |
| CMC | 5000 | 75 | 3235.5 | 3427 | 270.9 | 7.9 | 68.5 |
|  |  | 112.5 | 3618.6 |  |  |  |  |
| Sodium phosphate (pH 6.0) | 5000 | 75 | 4275.5 | 4423 | 208.7 | 4.7 | 88.5 |
|  |  | 112.5 | 4570.7 |  |  |  |  |

The results of measurement of botulinum toxin potency for each of the mixture compositions indicated that the percent recovery relative to the theoretical potency was 50% or higher. However, it was shown that the percent recovery measured for CMC was out of the range of the standard curve when a dilution factor of 112.5 was applied, and that the percent recovery values for CMC and sodium phosphate immediately after preparation were lower than the value measured for HSA or Tween 20.

Example 2: Selection of Precoating Material

To examine the change in the potency of the botulinum toxin according to whether a PLA (poly(lactic acid)) substrate is precoated and the kind of precoating material, an experiment was performed. 6.5 µl of a coating composition comprising each of HSA+NaCl, Tween 20, CMC and sodium phosphate (pH 6.0), mixed with botulinum toxin, was dropped onto a PLA substrate (non-coated; N), a 2% PVA precoated substrate (PVA), or a corresponding thickener coated substrate (e.g., when 1% HSA+1.8% NaCl was used as the thickener, a PLA substrate was also coated with 1% HSA+1.8% NaCl), and then dried overnight at room temperature. After completion of the drying, each of the substrates was put in 0.3 mL of 0.9% NaCl contained in a 1.5 mL tube, and the toxin was eluted at room temperature for 30 minutes. After completion of the elution, considering the case in which the potency of the botulinum toxin would remain 100% during recovery after dropping, each composition was diluted with a dilution factor of 83.3 and subjected to in vitro potency measurement. The results of the measurement are shown in Table 3 below and FIG. 1.

TABLE 3

| Preparation Example | Substrate precoating | Theoretical potency (U) | Dilution factor | Measured Potency (U) | Potency recovery (%) |
|---|---|---|---|---|---|
| HSA + NaCl | N | 5000 | 83.3 | 6195.2 | 123.9 |
| | PVA | 5000 | 83.3 | 6811.5 | 136.2 |
| | Corresponding thickener | 5000 | 83.3 | 6020.7 | 120.4 |
| Tween 20 | N | 5000 | 83.3 | N/D | Low |
| | PVA | 5000 | 83.3 | N/D | Low |
| | Corresponding thickener | 5000 | 83.3 | N/D | Low |
| CMC | N | 5000 | 83.3 | N/D | Low |
| | PVA | 5000 | 83.3 | 5950.5 | 119.0 |
| | Corresponding thickener | 5000 | 83.3 | N/D | Low |
| Sodium phosphate (pH 6.0) | N | 5000 | 83.3 | N/D | Low |
| | PVA | 5000 | 83.3 | 3883.3 | 77.7 |

(N/D; not detected)

As shown in Table 3 above and FIG. 1, when the potency during recovery after dropping was higher than the upper limit of the standard curve, it was expressed as N/D. Considering the results for sodium phosphate, it was shown that, when the substrate was coated with 2% PVA, the potency was stably maintained.

Tween 20 showed low potency in all the substrates, indicating that it is not suitable as a coating composition. In addition, CMC also showed no potency in all the substrates other than the PVA-precoated substrate, in the same manner as sodium phosphate.

Example 3: Selection of Optimum Thickener for Coating Composition Containing Botulinum Toxin To select a thickener to be contained in a coating composition from among candidate materials, each of eight coating candidate materials was prepared at 2× concentration (2% CMC, 1% SA, 1% HA, 1% MC, 1% HEC, 2% PVP, 1% HSA+1.8% NaCl, and 0.05M phosphate), and mixed with a botulinum toxin 2× concentration solution (5,000 U/3.25 µl) at a ratio of 1:1. Then, 6.5 µl of each of the prepared solutions was dropped onto a 2% PVA-precoated substrate, and then dried overnight at room temperature. After completion of the drying, each of the substrates was put in 0.3 mL of 0.9% NaCl contained in a 1.5 mL tube, and the toxin was eluted at room temperature for 30 minutes. After completion of the elution, considering the case in which the potency of the botulinum toxin would remain 100% during recovery after dropping, each coating solution was diluted with a dilution factor of 83.3 and subjected to in vitro potency measurement. The results of the measurement are shown in Table 4 below and FIG. 2.

TABLE 4

| Kind of coating solution | | n | Measured potency (U) | Average of measured potency values | Total SD | Total RSD | Average of total recovery values (%) |
|---|---|---|---|---|---|---|---|
| 1. CMC | | 1-1 | 4232.3 | 4004.4 | 177.7 | 4.4 | 80.1 |
| | | 1-2 | 4057.8 | | | | |

TABLE 4-continued

| Kind of coating solution | | n | Measured potency (U) | Average of measured potency values | Total SD | Total RSD | Average of total recovery values (%) |
|---|---|---|---|---|---|---|---|
| | | 2-1 | 3877.9 | | | | |
| | | 2-2 | 3849.6 | | | | |
| 2. SA | | 1-1 | 3412.6 | 3356.6 | 51.4 | 1.5 | 67.7 |
| | | 1-2 | 3338.3 | | | | |
| | | 2-1 | 3381.0 | | | | |
| | | 2-2 | 3294.6 | | | | |
| 3. HA | | 1-1 | 3216.0 | 3193.5 | 72.5 | 2.3 | 63.9 |
| | | 1-2 | 3086.3 | | | | |
| | | 2-1 | 3245.7 | | | | |
| | | 2-2 | 3226.1 | | | | |
| 4. MC | | 1-1 | 4494.5 | 4507.2 | 10.1 | 0.2 | 90.1 |
| | | 1-2 | 4518.9 | | | | |
| | | 2-1 | 4509.8 | | | | |
| | | 2-2 | 4505.7 | | | | |
| 5. HEC | | 1-1 | 4627.1 | 4356.6 | 183.2 | 4.2 | 87.1 |
| | | 1-2 | 4286.5 | | | | |
| | | 2-1 | 4221.3 | | | | |
| | | 2-2 | 4291.4 | | | | |
| 6. PVP | | 1-1 | 4097.1 | 4137.5 | 83.1 | 2.0 | 82.8 |
| | | 1-2 | 4165.6 | | | | |
| | | 2-1 | 4048.2 | | | | |
| | | 2-2 | 4239.2 | | | | |
| 7. Sodium phosphate | | 1-1 | 2915.0 | 2891.0 | 81.4 | 2.8 | 57.8 |
| | | 1-2 | 2787.1 | | | | |
| | | 2-1 | 2982.6 | | | | |
| | | 2-2 | 2879.5 | | | | |
| 8. HSA + NaCl | | 1-1 | 5044.6 | 4769.7 | 216.7 | 4.5 | 95.4 |
| | | 1-2 | 4837.7 | | | | |
| | | 2-1 | 4567.2 | | | | |
| | | 2-2 | 4629.2 | | | | |

CMC (carboxymethylcellulose sodium salt)
SA (sodium alginate)
HA (hyaluronic acid 1,000 kDa)
MC (methyl cellulose)
HEC (hydroxyethyl cellulose)
PVP (polyvinyl pyrrolidone)
Sodium phosphate Two samples (sample 1 and 2) per test group were prepared, and toxin eluted from each of the samples was measured twice. As a result, as can be seen in Table 4 above, it was shown that, among the coating compositions, the percent recovery relative to the theoretical potency of each of CMC, MC, HEC, PVP, and HSA+NaCl was as high as 80% or above. Particularly, MC and HSA+NaCl showed a high potency recovery of 90% or above. In addition, SA and HA also showed an average potency recovery of 60% or above, which was higher than that shown by sodium phosphate.

Example 4: Selection of Optimum Stabilizer for Coating Composition Containing Botulinum Toxin To select a stabilizer to be contained in a coating composition among candidate materials, each of coating compositions prepared as shown in Table 5 below was mixed with a botulinum toxin 2× concentration solution (5,000 U/3.25 µl) at a ratio of 1:1, and 6.5 µl of each of the prepared solutions was dropped onto a 2% PVA-precoated substrate, and then dried at room temperature overnight. After completion of drying, each of the substrates was placed in 0.3 mL of 0.9% NaCl contained in a 1.5 mL tube, and the toxin was eluted at room temperature for 30 minutes. After completion of elution, considering the case in which the potency of the botulinum toxin remains 100% during recovery after dropping, each coating solution was diluted at a factor of 83.3 and subjected to in vitro potency measurement.

TABLE 5

| Preparation Example | 2 × concentration |
|---|---|
| 1. PVP + Tre 10% | 2% PVP, 20% Tre |
| 2. PVP + Tre 15% | 2% PVP, 30% Tre |
| 3. PVP + Tre 20% | 2% PVP, 40% Tre |
| 4. PVP + Met 10 Mm | 2% PVP, 20 mM Met |
| 5. PVP + Met 20 mM | 2% PVP, 40 mM Met |
| 6. PVP + Met 30 mM | 2% PVP, 60 mM Met |
| 7. HEC + Tre 10% | 1% HEC, 20% Tre |
| 8. HEC + Tre 15% | 1% HEC, 30% Tre |
| 9. HEC + Tre 20% | 1% HEC, 40% Tre |
| 10. HEC + Met 10 mM | 1% HEC, 20 mM Met |
| 11. HEC + Met 20 mM | 1% HEC, 40 mM Met |
| 12. HEC + Met 30 mM | 1% HEC, 60 mM Met |
| 13. CMC + Tre 10% | 2% CMC, 20% Tre |
| 14. CMC + Tre 15% | 2% CMC, 30% Tre |
| 15. CMC + Tre 20% | 2% CMC, 40% Tre |
| 16. CMC + Met 10 mM | 2% CMC, 20 mM Met |
| 17. CMC + Met 20 mM | 2% CMC, 40 mM Met |
| 18. CMC + Met 30 mM | 2% CMC, 60 mM Met |
| 19. HSA + NaCl | 1% HSA, 1.8% NaCl |
| 20. Sodium phosphate | 0.05M sodium phosphate |

Tre (trehalose)
Met (methionine)

The experimental results in Table 6 indicated that PVP and HEC other than CMC showed a potency recovery of 90% or more relative to the value measured immediately after HSA preparation, in all stabilizer conditions. The results are shown in FIG. 3.

Example 5: Examination of Accelerated Stability of Coating Composition Containing Botulinum Toxin The long-term stabilities of mixtures of thickeners (SA, HA, PVP and HEC) and stabilizers (Tre and Met), selected based on the results of Examples 1 to 4 above, were examined.

To test the long-term stabilities of combinations of a SA or HA thickener and a stabilizer, PLA substrates were precoated with 2% PVA, and each of coating compositions prepared as shown in Table 6 below was mixed with a botulinum toxin 2× concentration solution (5,000 U/3.25 µl) at a ratio of 1:1. 6.5 µl of each of the mixtures was dropped onto each of the PLA substrates, and then dried overnight at room temperature. After completion of the drying, each of the substrates was put in 0.3 mL of 0.9% NaCl contained in a 1.5 mL tube, and the percent potency recovery for each substrate was measured up to day 8. Because the coating compositions themselves, which comprise mixtures of thickeners and stabilizers in various combinations, would affect the measurement of the botulinum toxin potency, the potency measured for each test group on day 1 was taken as a reference value 100, and the potency measured on day 8 was expressed relative to the potency measured on day 1. The results are shown in FIG. 4. The test results indicated that most of the test groups comprising the SA or HA thickener maintained a potency of 50% or higher relative to the day-1 potency up to day 8.

TABLE 6

| Preparation Example | Remarks |
|---|---|
| 1. SA + Tre 10% | 0.5% Sodium Alginate, 10% Trehalose |
| 2. SA + Tre 15% | 0.5% Sodium Alginate, 15% Trehalose |
| 3. HA + Tre 10% | 0.5% Hyaluronic acid, 10% Trehalose |
| 4. HA + Tre 15% | 0.5% Hyaluronic acid, 15% Trehalose |
| 5. HA + Tre 20% | 0.5% Hyaluronic acid, 20% Trehalose |
| 6. HA + Met 10 mM | 0.5% Hyaluronic acid, 10 mM Methionine |

TABLE 6-continued

| Preparation Example | Remarks |
|---|---|
| 7. HA + Met 20 mM | 0.5% Hyaluronic acid, 20 mM Methionine |
| 8. HA + Met 30 mM | 0.5% Hyaluronic acid, 30 mM Methionine |
| 9. PVP + Tre 10% | 1% Polyvinyl pyrrolidone, 10% Trehalose |
| 10. PVP + Met 20 mM | 1% Polyvinyl pyrrolidone, 20 mM Methionine |
| 11. HAS + NaCl | 0.5% Human Serum Albumin, 0.9% Sodium Chloride |
| 12. NaP | 25 mM Sodium Phosphate pH 6.0 |

In addition, in order to test the long-term stabilities of combinations of a PVP or a HEC thickener and a disaccharide or an amino acid stabilizer, botulinum toxin coating compositions were prepared and dropped in the same manner as the test performed on the SA and HA thickeners, and then an accelerated stability test was performed at 37° C. for 5 weeks. Trehalose (Tre), or sucrose (Suc) was used as a disaccharide stabilizer, and methionine (Met) or glycine (Gly) was used as an amino acid stabilizer. For an accurate comparison of measured values, the potency immediately after preparation of each of the samples was taken as a reference value (100%), and the potencies at varying time points during 5 weeks were expressed relative to the reference value. In addition, the value of a standard product that is a positive control in the BoTest test was applied to minimize the error between the tests. The results of the test are shown in Table 7 below and FIG. 5.

TABLE 7

| Preparation Example | Immediately after preparation | 1 day | 8 days | 22 days | 36 days |
|---|---|---|---|---|---|
| 1% PVP | 100.0 | 92.3 | 71.2 | 61.1 | N/D |
| 1% PVP + 10% Tre | 100.0 | 107.9 | 85.1 | 70.2 | 57.2 |
| 1% PVP + 30% Suc | 100.0 | 239.5 | 154.7 | 154.7 | 68.1 |
| 1% PVP + Met 20 mM | 100.0 | 108.4 | 105.9 | 87.7 | 55.0 |
| 1% PVP + Gly 20 mM | 100.0 | 79.1 | N/D | N/D | N/D |
| 0.5% HEC | 100.0 | 80.7 | 65.2 | N/D | N/D |
| 0.5% HEC + 10% Tre | 100.0 | 92.5 | 88.9 | 66.0 | 53.4 |
| 0.5% HEC + 30% Suc | 100.0 | 81.6 | 55.7 | 58.9 | 53.1 |
| 0.5% HEC + Met 20 mM | 100.0 | 104.0 | 59.9 | N/D | N/D |
| 0.5% HEC + Gly 20 mM | 100.0 | 83.2 | N/D | N/D | N/D |
| HSA +NaCl | 100.0 | 112.7 | 86.0 | 61.5 | 45.6 |
| Sodium phosphate (pH 6.0) | 100.0 | 105.2 | 89.4 | 67.9 | N/T |

(N/D: not detected, N/T: not tested)

The test results indicated that the combination using PVP, or HEC as a thickener, and the disaccharide, or methionine as the stabilizer are the optimal stabilized combinations for preparation of botulinum toxin coating compositions, compared to the positive control HSA.

Example 6: Confirmation of Coating Uniformity of Coating Composition Containing Botulinum Toxin Coating uniformity of compositions for coating on substrates such as microneedles is very important. In addition, since the composition comprises botulinum toxin, the titer stability of the botulinum toxin should be ensured. Thus, a substrate was precoated with 2% PVA, the substrate was coated with a thickener and stabilizer combination composition which was evaluated as having excellent titer stability of botulinum toxin in Example 5, and coating uniformity was evaluated by average number of pixels and magenta ratio. More specifically, the picture was set to CMYK instead of RGB, the size of the needle was equally adjusted in each picture, the back background of the picture was deleted except needle, the total area of the needle was measured, and the average number of pixels and magenta ratio were measured in the stained area of the needle. The results are shown in Table 8, Table 9, and FIG. 6.

TABLE 8

| Preparation Example | Average number of pixels |
|---|---|
| HEC + Suc, once for 10 seconds | 392 |
| PVP + Tre, once for 10 seconds | 366 |
| HEC + Suc, once for 15 seconds | 605 |
| PVP + Tre, once for 15 seconds | 402 |

TABLE 9

| Preparation Example | Magenta ratio (%) | | | | | |
|---|---|---|---|---|---|---|
| HEC + Suc, once for 10 seconds | 84 | 90 | 88 | 92 | 89 | 93 |
| PVP + Tre, once for 10 seconds | 47 | 81 | 66 | 81 | 71 | 79 |

The experimental results showed that the HEC+Suc combination had a higher average number of pixels than the PVP+Tre combination when the microneedle was coated for 10 or 15 seconds. In addition, the ratio of magenta dyed area to total microneedle area was significantly higher in the HEC+Suc combination when the same time was applied (The average of HEC+Suc combination: 89%, and the average of PVP+Tre combination: 71%). As a result, it was found that the coating using the HEC+Suc combination is more uniform than using the PVP+Tre combination.

From the results of Examples 1 to 6 above, it could be found that, in fabrication of stabilized microstructures enabling a botulinum toxin to be accurately administered to a desired position at a precisely controlled concentration without causing discomforts such as pain. Carboxymethyl cellulose sodium salt, sodium alginate, hyaluronic acid, methyl cellulose, hydroxyethyl cellulose, polyvinyl pyrrolidone, or combinations thereof are effective as thickeners. Furthermore, trehalose, sucrose, a combination of trehalose and sucrose, methionine, sodium phosphate, a mixture of human serum albumin and sodium chloride, or combinations thereof are remarkably effective as stabilizers.

INDUSTRIAL APPLICABILITY

The present invention relates to microstructure formulation techniques for botulinum toxin. The microstructure formulation techniques for botulinum toxin according to the present invention make it possible to precisely control the concentration of botulinum toxin and to alleviate the pain occurring when botulinum toxin is administered into the human body, and also enable botulinum toxin to be accurately administered to a desired position. Thus, the present invention is expected to greatly contribute to the safe and convenient medical use of botulinum toxin.

The invention claimed is:

1. A microstructure selected from the group consisting of a microneedle, a microblade, a microknife, a microfiber, a microspike, a microprobe, a microbarb, a microarray, and a microelectrode, wherein the microstructure is coated with a botulinum toxin composition comprising a botulinum toxin selected from the group consisting of botulinum toxin type A, B, C, D, E, F and G, a thickener and a stabilizer, wherein the thickener is any one or more selected from the group consisting of carboxymethyl cellulose sodium salt, sodium alginate, hyaluronic acid, methyl cellulose, hydroxyethyl cellulose, and polyvinyl pyrrolidone, and wherein the stabilizer is trehalose, sucrose, or a combination of trehalose and sucrose, wherein the microstructure is precoated with a polymer compound or polyvinyl alcohol.

2. A method for coating a microstructure with a botulinum toxin composition, the method comprising the steps of: (a) precoating the microstructure, wherein the microstructure is selected from the group consisting of a microneedle, a microblade, a microknife, a microfiber, a microspike, a microprobe, a microbarb, a microarray, and a microelectrode with a polymer compound or polyvinyl alcohol; (b) mixing a botulinum toxin selected from the group consisting of botulinum toxin type A, B, C, D, E, F and G, a thickener and a stabilizer to obtain a mixture; and (c) dipping the precoated microstructure of step (a) into the mixture of step (b), followed by drying, wherein the thickener is any one or more selected from the group consisting of carboxymethyl cellulose sodium salt, sodium alginate, hyaluronic acid, methyl cellulose, hydroxyethyl cellulose, and polyvinyl pyrrolidone, and wherein the stabilizer is trehalose, sucrose, or a combination of trehalose and sucrose.

* * * * *